United States Patent
Buono et al.

(10) Patent No.: US 8,401,621 B2
(45) Date of Patent: Mar. 19, 2013

(54) METHOD AND DEVICE OF DETECTING, LOCATING AND/OR ANALYZING A RADIOACTIVE SOURCE(S) IN A MATERIAL, E.G. A BIOLOGICAL TISSUE

(75) Inventors: Stefano Buono, Thoiry (FR); Iris Desforges, Genève (CH); Eugène Grigoriev, Chene-Bourgeries (CH); Roberto Rocca, Cagliari (IT)

(73) Assignee: Forimtech S.A., Geneva (CH)

( * ) Notice: Subject to any disclaimer, the term of this patent is extended or adjusted under 35 U.S.C. 154(b) by 487 days.

(21) Appl. No.: 12/300,175

(22) PCT Filed: May 11, 2006

(86) PCT No.: PCT/EP2006/005828
§ 371 (c)(1),
(2), (4) Date: Jan. 7, 2011

(87) PCT Pub. No.: WO2007/131536
PCT Pub. Date: Nov. 22, 2007

(65) Prior Publication Data
US 2011/0196234 A1 Aug. 11, 2011

(51) Int. Cl.
*A61B 6/00* (2006.01)

(52) U.S. Cl. ........................................ 600/431; 600/436

(58) Field of Classification Search .......... 600/407–436, 600/473–480
See application file for complete search history.

(56) References Cited

U.S. PATENT DOCUMENTS

| | | | |
|---|---|---|---|
| 4,788,436 A | 11/1988 | Koechner | |
| 5,374,824 A * | 12/1994 | Chaney et al. | 250/363.02 |
| 7,652,259 B2 * | 1/2010 | Kimchy et al. | 250/370.08 |
| 2003/0187349 A1 * | 10/2003 | Kaneko et al. | 600/425 |
| 2006/0237652 A1 * | 10/2006 | Kimchy et al. | 250/363.02 |

FOREIGN PATENT DOCUMENTS

| | | |
|---|---|---|
| FR | 2 693 803 | 1/1994 |
| FR | 2 763 700 | 11/1998 |
| WO | WO 00/37967 | 6/2000 |

OTHER PUBLICATIONS

International Search Report for PCT/EP2006/005828, mailed Jan. 4, 2007.

\* cited by examiner

*Primary Examiner* — Sanjay Cattungal
(74) *Attorney, Agent, or Firm* — Harris Beach PLLC

(57) ABSTRACT

A method of detecting and/or analyzing a radioactive source emitting charged or neutral particles in a biological tissue, consisting essentially in using scintillating fibers having particular ratios of length or diameter to range of the particles emitted by the source; scanning the surface of the material with the detection rod; collecting by means of a SiPM, the scintillation light output generated by the particles having interacted with the scintillating fibers and emitted at the outlet end; optionally selecting signals corresponding to the particles entering the scintillating fibers in a substantially axial direction, that eliminates the particles from certain angles between the axis of the scintillating fiber and the direction of the particles entering the scintillating fiber, correlating the scintillation light output and the selected signals to the presence of a source of radiation located in the material to be analyzed; and optionally communicating these data to the user.

32 Claims, 2 Drawing Sheets

Figure 1:
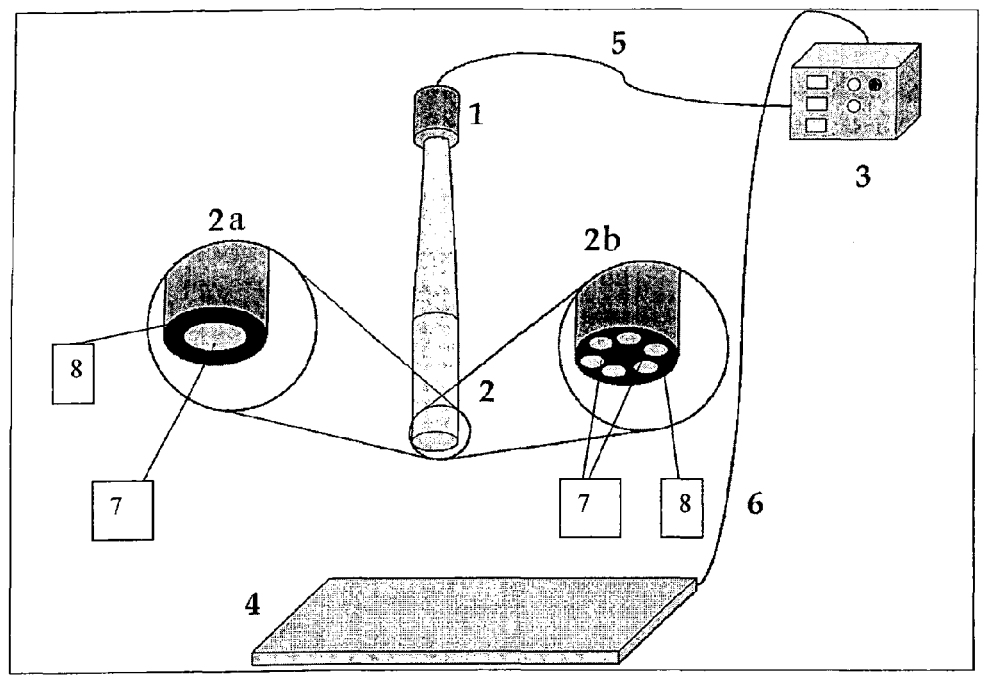

METHOD AND DEVICE OF DETECTING, LOCATING AND/OR ANALYZING A RADIOACTIVE SOURCE(S) IN A MATERIAL, E.G. A BIOLOGICAL TISSUE

This application is the U.S. national phase of International Application No. PCT/EP2006/005828, filed 11 May 2006, which designated the U.S., the entire contents of which are hereby incorporated by reference.

FIELD OF THE INVENTION

The general field of the invention is that of the detection of radiations by means of any appropriate devices, particularly those comprising small probes capable of being used in pre-operative medical diagnostics, in surgery [preferably radio-guided surgery, especially neurosurgery or oncological surgery (intra-operative tumor locating)], in any bio-medical study, or in any non-invasive intra-cavity, transcutaneous or intravascular detection of radioactive tracers in any medium, in particular in biological tissues (radiolabelled biological tissues).

More precisely, the invention relates to the analysis of materials, particularly biological objects (e.g. tissues), by the detection of primary or secondary ionising radiation, (particularly positron), particularly positron radiation, emitted by a material, particularly a biological tissue, which is radioactive but preferably radiolabelled with radiopharmaceutical compounds in the case of biological tissue.

Without implying a limitation, the invention relates more specifically to the tools, particularly the devices comprising probes, to the principle of working of these tools (i.e the method of detecting, locating and/or analyzing a radioactive source(s) in a material) and to the diagnostic, study and surgical practices, especially oncological surgical practices, diagnostic, metabolic or pharmaceutical studies in which said tools are applied.

STATE OF THE ART

In fact, it is known that the surgeon who practices the excision or resection of diseased biological tissues, such as tumors or abscesses, has a great need for assistance in detecting and delimiting the diseased areas when performing surgery, it being so difficult for him to distinguish the diseased areas from the healthy areas visually. This difficulty is all the greater in oncological surgery, given that numerous small tumors can be disseminated in healthy tissues.

Radioguided surgical techniques have therefore been known for a long time and consist in injecting patients with a radioactive isotope that emits β radiation (positrons and/or electrons) and/or γ radiation and has the property of binding preferentially to the diseased areas, e.g. the tumors, via their carrier molecules. The surgeon then uses a peroperative manual probe sensitive to the radioactivity emitted by the radiolabelled carrier molecules.

This type of radioguided surgery is thus commonly employed for the treatment of lung cancers, melanomas, thyroid cancer, neuroendocrine cancer and benign tumors such as, inter alia, parathyroid hyperplasias or osteoid osteomas. On the other hand, this radioguided surgical technique using a radiosensitive peroperative manual probe is still undergoing evaluation for applications in the treatment of tooth neck or colon cancers.

Radiosensitive peroperative manual probes are also of great value in the context of the technique known as "sentinel lymph node (SLN) biopsy". This cancer diagnostic technique is based on the sentinel node concept, according to which the state of the sentinel lymph node of the nodal regional lymphatic basin draining a primary tumor is an indication of the cancerous or non-cancerous state of the whole of the nodal lymphatic region in question. If the sentinel node is affected, the whole region is affected, and vice-versa.

Hitherto, the radiosensitive peroperative probes most widely used routinely for radioguided surgery, especially SLN biopsy, have been γ probes suitable for detecting γ radiation (γ ray or photon). However, γ radiation has the disadvantage of a relatively long range within biological tissues, which creates a considerable background. It is thus difficult to differentiate the tumoral areas from the healthy tissues. Moreover, this contamination by the γ radiation background makes it difficult, if not impossible, to detect close radiolabelled tumoral areas.

Peroperative manual probes sensitive to β radiation (positron and/or electron) have therefore been developed as possible alternatives to γ probes.

Insofar as β particles have a relatively short range in tissues, peroperative manual probes whose principle is based on detecting these β emissions are potentially much more sensitive in the delimitation and location of focused cancerous areas than more standard probes which operate by the detection of highly penetrating γ radiation.

Positron-emitting isotope markers with a high affinity for cancerous tissues are known, an example being $^{18}$F-labeled 2-fluorodeoxy-D-glucose (FDG). $^{18}$F-labeled FDG is a specific marker for a carbohydrate hypermetabolism indicative of malignant tissues or inflammatory tissues. This marker is already used in diagnostic medicine for mapping the spread of a cancer with the aid of complex and expensive positron-detecting equipment (PET (Positron Emission Tomography) camera). It may be noted incidentally that this cumbersome "whole body" detection equipment cannot compete with compact devices comprising novel peroperative probes. In fact, apart from its cost, this equipment has the disadvantages that the detection threshold for tumoral nodules is limited to about 8 mm and that it is incapable of being used in peroperative mode because of its bulk and the slowness with which it analyzes. Peroperative manual probes therefore incontestably have their place among the technical means of assisting doctors in the treatment of diseases such as cancers.

However, there are numerous technical obstacles along the path leading to the optimization of peroperative manual devices (probes) for assisting surgery (radioguided surgery) which operate on the principle of the detection of positrons emitted by radioactive elements such as tumor tracers of the $^{18}$F-labeled FDG type. In fact, these radiopharmaceutical markers are radioactive isotopes that emit particularly unstable positrons which, after interaction with an electron from the medium in which they are present, each generate two 511 keV annihilation γ photons, emitted simultaneously, along the same line but in opposite directions. Now, it is these annihilation γ photons which have to be selectively and sensitively detected since they are the fruits of the hyperactivity of the radiolabelled targets (e.g. cancerous tissues).

However, the contrast between the radiolabelled areas with high isotope concentration (tumoral) and the non-radiolabelled (e.g. healthy) areas is impaired by a background radiation, and a percentage of lower-energy photons derived from Compton diffusion, i.e. the interaction of the photons with the patient's whole body and subsequently their change in direction and decrease in energy in the patient's whole body outside the radiolabelled target areas.

TECHNICAL PROBLEM

It is therefore apparent that one of the fundamental technical problems is to discriminate between on the one hand the useful detection radiation, and on the other hand the stray background radiation.

In addition to the rightsizing and the compactness, another difficulty to overcome is to provide peroperative manual probes reliable and sensitive, that makes it possible to localize with accuracy, sources of radiation (e.g. clusters of radioactive substances in any biological tissue) of small size, for instance less than or equal to 10 mm or to 8 mm or even 1 mm.

Other specifications are notably: easy use, structural and functional simplicity, ability for sterilization, low operating voltage, very high internal gain, safety, low price.

The WO-A-2005/114254 proposed improved peroperative positron probes, a improved method of analyzing materials, particularly biological tissues, by the detection of positrons emitted by a material, preferably a radioactive—advantageously radiolabelled—biological tissue, which makes it possible reliably, sensitively, selectively and economically to disclose target materials, particularly radiolabelled biological tissues, e.g. cancerous tissues and an improved device for implementing such a method.

Said method comprises the following steps consisting in: placing at least two opposing detectors on either side of a mass of material to be analysed; detecting, in coincidence in each detector, a Compton electron generated, by means of the Compton scattering mechanism, from the interaction with one of the two incident photons resulting from the annihilation between a positron emitted by the mass of material to be analysed and an electron; selecting the coincident detection signals, namely the signals for each of which the detection of a Compton electron in a detector coincides temporally with the detection of a Compton electron in the other opposing detector; counting the selected signals such as to gather information that is representative of the quantity of positrons emitted by the mass of material to be analysed; and, optionally, communicating the aforementioned information to the user. WO-A-2005/114254 also relates to the device [peroperative (clamp) probe] used to implement the method. The invention according to WO-A-2005/114254 is suitable for the identification and excision of tumours.

OBJECTS OF THE INVENTION

One of the essential objects of the present invention is to propose an alternative to the peroperative (clamp) probes and to the method according the WO-A-2005/114254, while trying to improve the performance characteristics in terms i.a of background, miniaturization & compactness, increasing the sensitivity and selectivity towards small sources of radiation, detecting/locating/analyzing radioactive or radiolabelled zones (tumoral formations) of millimetric or even submillimetric dimensions, easy use, structural and functional simplicity, low price and considering notably the medical purposes: ability for sterilization, low operating voltage, very high internal gain, safety.

Another essential object of the invention is to improve radioguided surgical practices, especially as regards oncological surgery.

Another essential object of the invention is to develop a method of detecting/locating/analyzing materials, particularly biological tissues, by the detection of charged or neutral particles (especially a positron emitter) emitted by a material, preferably a radioactive—advantageously radiolabelled—biological tissue, which makes it possible reliably, sensitively, selectively and economically to disclose target materials, particularly radiolabelled biological tissues, e.g. cancerous tissues.

Another essential object of the invention is to propose a device for implementing such a method.

Another essential object of the invention is to provide a method and a device for precisely locating small tumoral areas within all types of biological tissues.

Another essential object of the invention is to provide a method and a device for locating, detecting and identifying cancerous lesions, enabling the surgeon easily to:
- remove all doubt about the cancerous or non-cancerous nature of a lesion,
- detect the spread of a tumor invisible to the naked eye or by palpation,
- analyze the lymphatic spread of a tumor in vivo and in real time for major prognostic and therapeutic purposes: decision-making aid, modification of the initially planned surgery (decreasing or increasing the amplitude of the exeresis),
- analyze surgical slices in real time and in vivo,
- scan the operative field at the end of an intervention so as not to leave in place tumoral tissue which would have gone unnoticed with conventional procedures.

Another essential object of the invention is to propose a method and a device for detecting/locating and identifying tumoral areas, making it possible considerably to optimize the advantage-to-disadvantage ratio of surgery.

Another essential object of the invention is to propose a method and a device for detecting/locating and analyzing (identifying) tumoral areas, making it possible to delimit tumors in vivo and excise them with precision, and also to apply tumor detection techniques in the sentinel lymph node (SLN) without the need for biopsy.

Another essential object of the invention is to propose a method and a device, as defined above, for distinguishing between on the one hand β radiation emitted by a tissue radiolabelled with isotopes emitting β radiation in that part of the tissue targeted by the detector, and on the other hand β and γ radiation emitted by tissue not targeted by the detector.

Another essential object of the invention is to propose a method and a device for detecting/locating and analyzing (identifying) in the purpose of pre-operative medical diagnostics, of intra-operative radiolabeled tissues/organs localization in surgery, preferably radio-guided surgery (neuro or oncosurgery), of any bio-medical study, of non-invasive intra-cavity or of transcutaneous or intravascular detection/localization/analyzing of radiolabelled biological tissues.

DESCRIPTION OF THE INVENTION

The Method

These and other objects are achieved by the present invention, which relates first and foremost to a method of detecting, locating and/or analyzing a radioactive source(s) emitting charged or neutral particles in a material, particularly a biological tissue, characterized in that it consists essentially in:
- placing one of the ends ($1^{st}$ end) of at least one detection rod made of at least one scintillating fiber (preferably a substantially straight one), on or near the surface of the material to be analyzed, so as to enable the charged or neutral particles to enter the scintillating fiber(s); said scintillating fiber(s) having a ratio L (Length)/r (range of the charged particles emitted by the source or produced in surrounding medium as secondary products) greater than or equal to 2, preferably greater than or equal to 10, and more preferably comprised between 50 and 200;

scanning said surface with the detection rod;

collecting the scintillation light output ($SL_o$) generated by the charged or neutral particles having entered and interacted with the scintillating fiber(s) and emitted at least partially at the opposite end ($2^{nd}$ end or outlet end) of the detection rod;

optionally selecting at least some of the signals of scintillation light corresponding to $SL_o$;

correlating $SL_o$, and optionally the selected signals, to the presence of a source of radiation located in the mass of the material to be analyzed;

optionally correlating the intensity of the selected signals to the mass and/or the volume of the detected source of radiation, for the purpose of analysis;

optionally communicating these data to the user.

Such a method using scintillating fiber's with particular ratio L/r and coupled with means for collecting the scintillating signals produced by the particles interacted with the fiber(s), makes it possible to detect locally concentrations (in steady state or dynamics) of isotopic tracers emitting short range ionizing particles (beta, positrons, alpha, . . . ). In this case the background is stopped by the parts of the material which have less radioactivity than the possible source of radiations of the material, for example by the surroundings tissues in the case where the material is a biological tissue.

Preferably, the scintillating fiber(s) has a ratio d/r, with d representing the diameter of the scintillating fiber and r the range of the detected particles, which is lower than or equal to 1, preferably comprised between 0.01 and 1, more preferably between 0.05 and 0.5, and more preferably between 0.1 and 0.3.

In a preferred embodiment, the method according to the invention comprises the following steps:

comparing $SL_o$ with a threshold $SL_t$ corresponding to a given quantity of energy $E_t$ deposited by the particles on a length $l_t$ ($l_t$ being lower than or equal to the range r of said particles) in the scintillating fiber, said length $l_t$ being correlated to a discrimination angle $\alpha_t$ which is the angle between the axis of the scintillating fiber and the direction of the particles entering the scintillating fiber;

selecting the signals of scintillation light for which $SL_o$ is greater than or equal to $SL_t$, said selected signals corresponding essentially to the particles entering the scintillating fiber(s) in a substantially axial direction, that is to say eliminating the particles:

which angle $\alpha_p$, that is the angle between the axis of the scintillating fiber and the direction of the particles entering the scintillating fiber, is greater than $\alpha_t$ ($\alpha_p > \alpha_t$), then which length $l_p$ is lower than $l_t$ ($l < l_t$), and thus finally which quantity of energy $E_p$ deposited by the particles on a length $l_p$ in the scintillating fiber is lower than $E_t$ ($E_p < E_t$);

correlating the selected signals to the presence of a source of radiation located in the mass of the material to be analyzed and substantially in the axis of the detection rod.

According to this preferred embodiment invention, the background is eliminated/discriminated as a priority by implementing a new way of discrimination of background in the method of localization of a source of radiation, using a device composed of a probe included scintillating fibers of specific ratio L/r (preferably directly) coupled to means for collecting and treating the scintillation light output $SL_o$ coming from the scintillating fiber(s). One of the essential features of this embodiment is to provide a discrimination of the particles which are substantially in the direction of the fiber(s) with $\alpha_p < \alpha_t$ from the particles which are not substantially in the direction of the fiber(s) with $\alpha_p > \alpha_t$.

Instead of traditional method of discrimination background by shielding the scintillation detector with high-Z material (lead, tungsten, etc.), which after all cannot be envisaged because of the miniaturization constraints imposed on such devices, and which makes the probe heavy and bulky, it is proposed according to the invention to use scintillator in form of fibers with specific L/r and to eliminate noise by combining a suitable fiber geometry with the use of an opportune energy threshold.

Advantageously, $\alpha_t$ is lower than or equal to 45 ($\alpha_t \leq 45$), preferably lower than or equal to 30 ($\alpha_t \leq 30$), more preferably comprised between 0 and 10 ($0 \leq \alpha_t \leq 10$).

The directional sensitivity is also optimized when the scintillating fiber(s) has a ratio L (Length)/d (diameter) greater than or equal to 2, preferably greater than or equal to 5, and more preferably comprised between 10 and 500.

Charged particles either emitted directly from the source of radiation, or produced as secondary products in interactions of primary particles with the material of the probe or surrounding the source and/or the probe, produce ionization along the path while traversing or stopping in the scintillating fiber. Due for example to very high aspect ratio (length/diameter) of the fiber and to the small diameter compared to the particle range, the particles directed longitudinally deposit much more ionization losses inside the fiber than the ones traversing the fiber at large angle.

In the case where the particles are neutral particles and particularly gamma particles ($\gamma$-rays detection), the invention can use also the characteristics of the Compton interaction (in particular the angular distribution of the scattered electron). In this case the device is either used outside the patient body or, in case of internal use, it comprises a shielding of sufficient thickness to stop positions.

In this context where the particles comprise photons which interact with the scintillating fiber(s) with emission of secondary electrons which are the particles actually detected, a provision of the method of the invention is that $SL_o$ is compared with a minimum limit SLt related to a limit for the Compton scattering angle, in order to discriminate the photons which are essentially aligned with the fiber.

For example when the source of radioactive source contains positron emitter like $^{18}$F FDG, the $SL_t$ could correspond to a minimum energy greater or equal to 200 keV.

Preferably, the method comprise a step consisting in converting the optical signals of scintillation light output into electric signals.

Advantageously, the radioactive source(s) is (are) a cluster(s) of radioactive substances, in the method according to the invention. These radioactive substances either move or stay in the same place. In biological applications, they move for example when they are not fixed to a tissue or an organ, that is to say when they are in circulating fluids, like blood.

Preferably, the radioactive source(s) emit(s) charged and/or neutral radiations, particularly positron radiations.

More preferably, the material is a biological tissue, which is radiolabelled with a positron emitter.

In the context of onco-diagnostic, the method according to the invention, can be in a particular embodiment, a method wherein the material is a biological tissue, wherein the radioactive source(s) is(are) preferably a tumor(s), radiolabelled with radiopharmaceutical compounds and wherein the data communicated to the user are limited to the information according to which a source of radiation with a higher activity than the surroundings tissues is or is not detected, with the exception of any deductive medical or veterinary decision (purely intellectual exercise) such as diagnostic conclusions.

The Device

According to another of its features, the present invention relates to a device specifically for implementing the method referred to above. This is a device for detecting, locating and analyzing a radioactive source(s) in a material, particularly a biological tissue, characterized in that it includes:

at least one probe comprising:

at least one detection rod made of at least one scintillating fiber (preferably a substantially straight one), through which the possible charged or neutral particles coming from the radioactive source(s) can enter the scintillating fiber(s) and so interact with the fiber(s) to generate scintillation light (SL), said scintillating fiber having a ratio L (Length)/r (range of the charged particles emitted by the source or produced in surrounding medium as secondary products) greater than or equal to 2, preferably greater than or equal to 5, and more preferably comprised between 10 and 200, the scintillating fiber comprising:

one $1^{st}$ end designed so as to be placed on or near the surface of the material to be analyzed and so as to scan said surface, one body (preferably a substantially straight one) of length L and of diameter d, and capable, on the one hand, to interact with the charged or neutral particles coming from the radioactive source(s) to generate scintillation light (SL), and, on the other hand, to channel SL up to the $2^{nd}$ end, one $2^{nd}$ end or outlet end through which possible SL can be at least partially emitted;

at least one compact photosensor (preferably directly connected to the tip of the detection rod corresponding to the $2^{nd}$ end(s) of the scintillating-fiber(s), for collecting the possible scintillation light output ($SL_o$) and transforming it in (a) electrical signal(s) ($SL_{oe}$), optional means for comparing $SL_{oe}$ with a threshold $SL_t$, optional means for selecting at least some of the signals of scintillation light corresponding to $SL_{oe}$;

means for correlating $SL_{oe}$, and optionally the selected signals to the presence of a source of radiation located in the mass of the material to be analyzed;

optional means for correlating the intensity of the selected signals to the mass and/or the volume of the detected source of radiation, for the purpose of analysis;

optional means for communicating these data to the user.

Due to these novelties the new device is more sensitive and easy to operate compared to traditional devices, which usually consist of heavily shielded scintillator optically coupled via a fiber-optical guide to a vacuum photo-multiplier, positioned inside the control box.

Contrary to the peroperative (clamp) probe according to the WO-A-2005/114254, which correspond to invasive technics, the instant invention opens non-invasive new applications, like intra-cavity, transcutaneous or intravascular detection.

Moreover, this compact and economical device, is simple and reliable to operate. It makes it possible, in total safety, sensitively and selectively to identify radioactivity sources, particularly tissues radiolabelled e.g. with $^{18}$FDG, even for very small objects.

According to a preferred embodiment invention in which the background is eliminated/discriminated as a priority by implementing a new way of discrimination of background, namely the directional sensitivity, the device is composed of a probe included scintillating fibers of specific ratio L/r with one outlet tip for the radioactive particles and (preferably directly) coupled to means for collecting and treating the scintillation light output $SL_o$ coming from the scintillating fiber(s). One of the essential features of this embodiment is to provide a discrimination of the particles which are substantially in the direction of the fiber(s) with $\alpha_p < \alpha_t$ from the particles which are of substantially in the direction of the fiber(s) with $\alpha_p > \alpha_t$.

So, in this preferred embodiment, the device include:

means for comparing $SL_{oe}$ with a threshold $SL_t$ corresponding to a electrical signal correlated to a given quantity of energy $E_t$ deposited by the particles on a length $l_t$ ($l_t$ being lower than or equal to the range r of said particles) in the scintillating fiber, said length $l_t$ being correlated to a discrimination angle $\alpha_t$ which is the angle between the axis of the scintillating fiber and the direction of the particles entering the scintillating fiber, means for selecting the signals of scintillation light for which $SL_{oe}$ is greater than or equal to $SL_t$, said selected signals corresponding essentially to the radioactive particles entering the scintillating fiber(s) in a substantially axial direction, that is to say eliminating the particles:

which angle $\alpha_p$, that is the angle between the axis of the scintillating fiber and the direction of the particles entering the scintillating fiber, is greater than $\alpha_t$ ($\alpha_p > \alpha_t$), then which length $l_p$ is lower than $l_t$ ($l < l_t$), and thus finally which quantity of energy $E_p$ deposited by the particles on a length $l_p$ in the scintillating fiber is lower than $E_t$ ($E_p < E_t$);

and means for correlating the selected signals to the presence of a source of radiation located in the mass of the material to be analyzed and substantially in the axis of the detection rod.

In practice and advantageously, $\alpha_t$ is lower than or equal to 45 ($\alpha_t \leq 45$), preferably lower than or equal to 30 ($\alpha_t \leq 30$), more preferably comprised between 0 and 10 ($0\alpha_t \leq 10$).

Advantageously, the radioactive source(s) is (are) cluster(s) of radioactive substances either moving or staying in the same place.

In a particular embodiment, the radioactive source(s) emit(s) beta and for charged and/or neutral radiations, particularly positron radiations.

More particularly, the material to be analyzed by the invention's device is a biological tissue, which is radiolabelled with a positron emitter.

As mentioned above for the method of the invention, in the case where the particles are neutral particles and particularly gamma particles (γ-rays detection), the invention can use also the characteristics of the Compton interaction (in particular the angular distribution of the scattered electron). In this purpose, the device is characterized in that the particles comprise photons which interact with the scintillating fiber(s) with emission of secondary electrons which are the particles actually detected, and in that said device comprises means for comparing $SL_o$ with a minimum limit $SL_t$ corresponding to a maximum accepted scattering angle between the incoming photon and the emitted electron, and means for selecting the $SL_o$ greater than or equal to $SL_t$.

Naturally, the compared signals are the electrical signals corresponding to $SL_o$ and $SL_t$.

The probe (which is preferably a pen type probe) comprises 2 essential elements which are hereinafter described, namely the scintillating fiber(s) and preferably one photo-sensor.

Scintillating Fiber(s)

Concerning the scintillating fiber(s) of the device according to the invention, its (their) ratio d/r, with d representing the diameter of the scintillating fiber and r the range of the detected particles, which is lower than or equal to 1, preferably comprised between 0.01 and 1, more preferably between 0.05 and 0.5, and more preferably between 0.1 and 0.3.

Moreover, the scintillating fiber(s) has (have) a particular ratio L (Length)/d (diameter) greater than or equal to 2, preferably greater than or equal to 5, and more preferably comprised between 10 and 500.

Another interesting feature of the invention can be to use scintillating fiber(s) with specific chemical doping of the fiber core material.

Such specific chemical doping makes it possible to optimize the emission of photons of light (scintillation) in increased proportional quantities with respect to the ionization losses.

Preferably, the external surface of the scintillation fiber(s) comprise(s) at least one cladding designed so as to capture the scintillating light SL which is then at least partially channeled towards the outlet end of the scintillation fiber(s).

Due to special, for instance:
single or double-cladding,
reflective coating,
or wrapping of the fiber(s), a considerable fraction of this light is captured inside the fiber and transmitted towards its ends. So, a remarkable characteristic of the device of the invention is that the fraction [% w/w with respect to the whole quantity of SL] of SL captured and channeled inside the fiber(s) is greater than or equal to 5, preferably comprised between 5 and 30, and more preferably between 10 and 20.

In a particular embodiment, the fiber(s) is composed of a scintillating part optically connected to a transparent fiber with the purpose to extend its length without increasing sensitivity to background radiation.

In this embodiment, the fibers can be read out by one or several photo-sensors.

This particular embodiment makes it possible to use the probe at distant locations without increasing the background count and without significant losses of the scintillation light.

Concerning the constituent material of the scintillating fiber(s) used in the invention, it could either of organic nature or of inorganic nature. Optionally, the scintillating fiber(s) can include scintillating crystals.

Detection Rod

In a first embodiment, the detection rod of the probe includes only one scintillating fiber.

In a second embodiment, the detection rod of the probe includes a set of parallel fibers, preferably interspaced by a bulk material.

Photo-Sensor

Preferably, the photosensor is a single-photon sensitive avalanche photodiode operating in 'Geiger mode', i.e. above breakdown, said photosensor being preferably selected in the group of Silicon Photo-Multiplier (SiPM) comprising: the Metal-Resistive Layer-Silicon-Avalanche Photo Diode (MRS-APD), the Avalanche Photo Diode operating in Geiger mode (APDG), the Multipixel Avalanche Photodiode (MAPD) and the Single Photon Avalanche Diode (SPAD) array.

This photo-sensor is very compact, capable to detect single photons of scintillation light, has low operating voltage and very high internal gain. All these features allow to put it directly into the probe. Indeed, according to another remarkable feature, the photo-sensor is directly optically coupled with the scintillating fiber(s) of the detection rod.

The advantage of SiPM in comparison with any other alternative photo-sensors is their compactness, low cost, low operating voltage (25-50 V), high internal gain (up to $10^6$), single-photon sensitivity at room temperature.

Reflecting Means

Advantageously, the inlet end of the scintillating fiber(s) or of the detection rod comprise means for reflecting the scintillating light towards the outlet end of said scintillating fiber(s).

In practice, the means for reflecting the scintillating light can be constituted by at least a reflector which is designed so as to cover one of the ends (preferably the inlet end) of the scintillating fiber(s) or of the detection rod, so that finally all light is collected at the opposite end (the outlet end) where it is collected and treated viewed by at least one (preferably one) photo-sensor.

Additional Detector

According to a particular possibility for implementing the invention, the device comprises at least one additional detector (preferably comprising a slab) which is intended to be placed opposite to the detection rod of the probe with respect to the material to be analyzed, and operated in coincidence with the detection rod of the probe for background discrimination in case where the source of radiation emits two-particle emitting isotopes.

This corresponds to certain applications wherein the source of radiation emits more than one particle at once (for example—$F^{18}$), additional reduction of noise can be achieved by the introduction of an additional (e.g. a second) detector preferably with a larger acceptance preferably between 1 and 1000 cm² area, operating in coincidence with the first detector (detection rod) of the probe.

In a more particular embodiment wherein the source of radiation emits positrons, the device comprises:

at least one additional detector (preferably comprising a slab) which is intended to be opposite to the detection rod with respect to the material to be analyzed, each of the two detectors being capable of detecting a Compton electron produced, according to the Compton scattering mechanism, from interaction of one of the two incident photons resulting from annihilation between a positron emitted by the mass of material to be analyzed, and an electron;

means for selecting the coincident detection signals, namely the signals for each of which the detection of a Compton electron in a detector coincides temporally with the detection of a Compton electron in the other opposite detector;

means for counting the selected signals so as to acquire data correlated with the amount of positrons emitted by the mass of material to be analyzed, said means for selecting and means for counting belonging to a system for processing the signals produced by the detectors.

In practice, the means of selecting the coincident detection signals work in such a way that only the particles emitted from the region of interest between the probe and the second detector will generate a signal; therefore all background originating from surrounding medium will be eliminated.

In practice, the means of counting the selected signals work in such a way that only signals coming in temporal coincidence from both detectors will be counted as a useful signal.

This optional second detector which can be switched in coincidence with the probe, in case of two-photon emission (for example, in detection of FDG or other positron-emitting markers), provides additional significant reduction of background, since only events originating from the volume between the probe and the second detector will give signals. For more details about this particular technique of detection by coincidence, in case of two-photon emission (for example, in detection of FDG or other positron-emitting markers), we refer to the method and device as described in WO-A-2005/114254, which is herein incorporated by reference.

Other Means

The means for comparing $SL_{oe}$ with a threshold $SL_t$, the means for selecting the signals of scintillation light, the means for correlating the selected signals to the presence of a source of radiation located in the mass of the material to be analyzed and substantially in the axis of the detection rod; the optional means for correlating the intensity of the selected signals to the mass and/or the volume of the detected source of radiation, for the purpose of analyzing; the optional means for communicating these data to the user, are all known electronic means.

Electronic Control Box

In a preferred carrying out, the device of the invention includes at least two structural distinct essential entities, on the one hand, the probe and, on the other hand, an electronic control for collecting and treating the signals.

Advantageously, (a) the means for comparing $SL_{oe}$ with a threshold $SL_t$, (b) the means for selecting the signals $SL_{oe}$, (c) the means for correlating the selected signals to the presence of a source of radiation, (d) the optional means for correlating the intensity of the selected signals to the mass and/or the volume of the detected source of radiation and/or (e) the optional means for communicating these data to the user (preferably in visual and/or audible form), are integrated in a electronic control box which is structurally independent and can be distant from the probe, said electronic control box being connected to the probe by means of transporting the detection electrical signal(s) ($SL_{oe}$).

The connection between the probe(s) and the electronic control box can be done by any appropriate means, e.g. with wire or wireless. In practice, the device of the invention is characterized in that one or several probes are connected with the electronic control box by means of a long (thin) and flexible electrical cable, length of the cable being preferably in the range between 0.3 and 3 meters.

This implementation with a thin, long and flexible electrical cable is possible, thanks to high amplitudes of signals obtained from preferred SiPM photosensors, even from single-photoelectron pulses. Such an electrical cable is much more thin and flexible than optical light-guides used in existing devices.

The electronic control box can advantageously comprise front-end electronics, power supplies, data acquisition and user interface units. Naturally, it can also contain inputs for as many probes as needed for a particular application.

In an interesting variant, the electronic control box includes a system for processing the signals produced by the probe and optionally by the additional detector(s), this system comprising:

- at least one of the means (a), (b), (c) (d) & (e) as defined above;
- optionally means of amplifying these electrical signals,
- optionally at least one comparator,
- optionally at least one analogue-to-digital converter,
- optionally means of selecting the coincident detection signals, including:
  - elements for discriminating between the electrical signals to be processed according to a Compton electron detection energy threshold S, i.e. according to the intensity of the electrical signals,
  - and/or elements for discriminating between the electrical signals to be processed according to their length (duration),
  - at least one electronic module for sorting the coincident detection signals,
  - means of counting the selected signals.

As above described, the device according to the invention can also include a particular attachment which is at least one additional detector. This latter is advantageously connected to the electronic control box, also by any adapted means, and for instance by a long, thin and flexible electrical cable.

Remarkably, the electronic control box is capable to provide information on the presence of source of radiations in different positions inside or outside the material under analysis.

Applications of the Device

Due to the novelties introduced in background discrimination and in light-collection, the probe built according to the new technology (method/process) according to the invention, can be very compact, safe and simple in operation and relatively cheap. In the minimal configuration it consists just of one fiber, for instance, of e.g. 0.2-1 mm in diameter directly coupled to a photosensor (preferably a SiPM) of the same size. In this case it can be put inside a needle, a catheter or any other medical instrument.

In a first application, the device according to the invention is characterized in that the material is a biological tissue, in that the radioactive source(s) is(are) a tumor(s), radiolabelled with radiopharmaceutical compounds and in that the device is used in the purpose of pre-operative medical diagnostics or intra-operative tumor localization in surgery, preferably radio-guided surgery.

In a second application, the device according to the invention is characterized in that the material is a biological tissue radiolabelled with radiopharmaceutical compounds, and in that the device is used in the purpose of any bio-medical static or dynamic study, of non-invasive intra-cavity, transcutaneous or intravascular detection of radiolabelled biological tissues or of neurology and neurosurgery.

The Radioactive Source to be Detected

In the method or the device according to the invention, any type of radioelement can be considered.

In a particular embodiment, the radioactive marker of the material to be analyzed is selected from any molecules labelled with positron emitters from the group comprising $^{18}F$, particularly $^{18}F$-labeled 2-fluorodeoxyglucose (FDG), $^{15}O$, $^{11}C$, $^{13}N$, $^{124}I$, $^{126}I$, $^{77}Br$, $^{64}Cu$, $^{178}Ta$, $^{108}Ag$, $^{95m}Tc$, $^{88}Y$, $^{81m}Rb$, $^{68}Ga$, $^{66}Ga$, $^{63}Zn$, $^{65}Zn$, $^{58}Co$, $^{56}Co$, $^{52}Fe$, $^{52}Mn$, $^{52m}Mn$, $^{26}Al$, $^{22}Na$ and mixtures thereof.

DESCRIPTION OF A SPECIFIC EMBODIMENT OF THE METHOD AND OF THE DEVICE ACCORDING TO THE INVENTION

The invention will be understood more clearly with the aid of the following detailed description of a preferred but non-limiting Example of how to implement the method according to the invention and produce a device for implementing said method. This detailed description is given with reference to the attached drawing, in which:

FIG. 1 is a diagram showing the preferred embodiment of the device according to the invention, composed of two main independent and disconnectable entities, namely the "pen" type probe (1,2) and the electronic control box (3), as well as the attachment constituted by a second detector (4).

Figure 2:
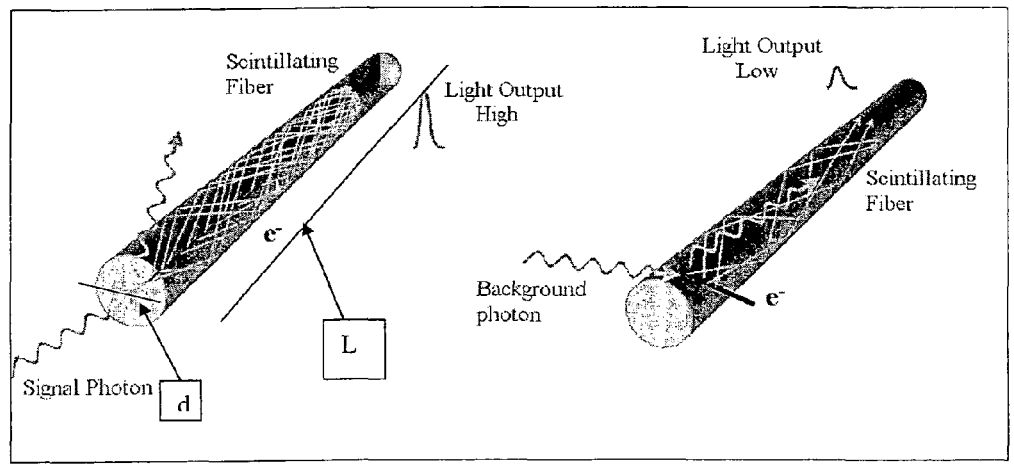

FIG. 2. is a schematic illustration of selective forward directional sensitivity of a scintillating fiber of the probe belonging to the device according to the invention.

Figure 3:
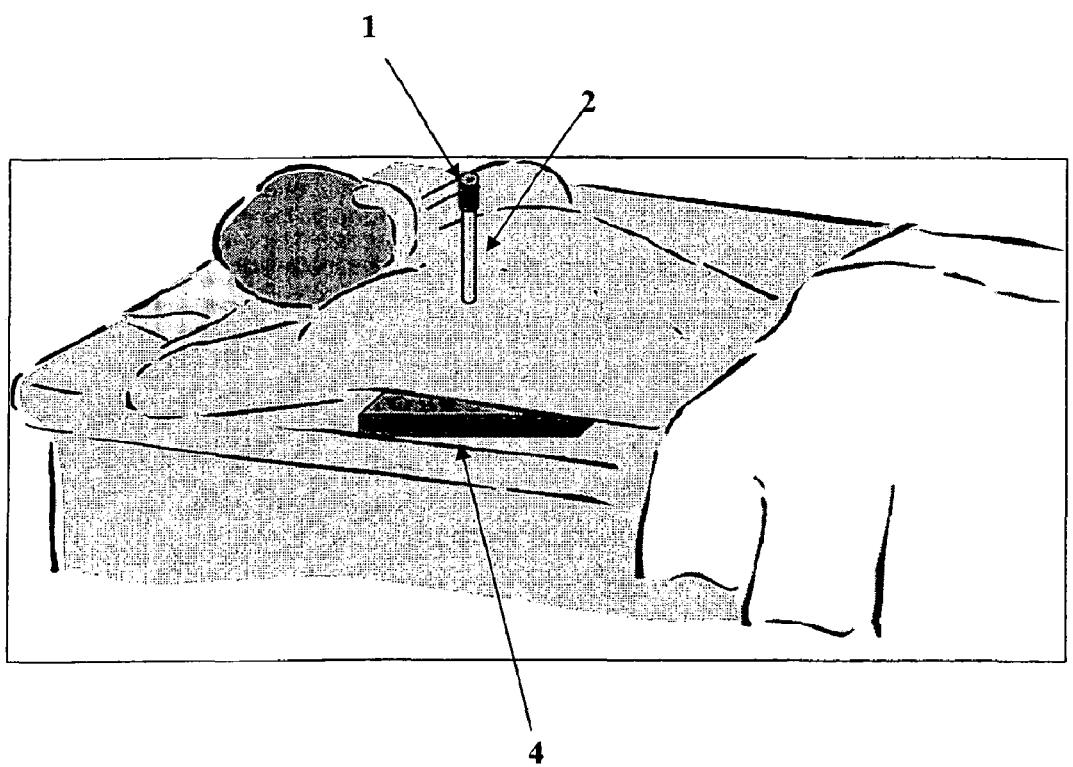

FIG. 3. is a schematic example of the use of the probe belonging to the device according to the invention, in a medical diagnostic, preoperative or intraoperative procedure.

The device showed on FIG. 1 is composed of:
a probe (1,2) made of a detection rod (2) and of a photo-sensor (1);
an electronic control box (3);
an optional second detector (4);
the probe (1,2) and the second detector (4) being connected to the electronic control box (3) by means of a flexible, thin and long electrical cable (5), (6) respectively (e.g. 2 meters).

The detection rod can be made of a single scintillating fiber (7) [FIG. 2a] or an array of fibers (7) [FIG. 2b].

The detection rod (2) of the probe has an elongated general form, similar to the form of a pen. The dimensions of said detection rod (2) are given by the ones of the scintillating fiber(s) (7) which are included in it.

The dimensions of the scintillating fiber (7) (shown on FIG. 2) are the length L and diameter d of the scintillating fiber (7).

In this example of implementing the invention,
the particles are photons and the detected Compton electrons
the parameters L, r (range), $\alpha_t$ (discrimination angle)=10, d, $SL_t$ (maximum limit for the secondary electrons) are:
L=10 cm, d=0.2 mm, r=1 mm, SLt=250 keV, $\alpha_t$=25 deg According to the invention, L/d is greater than or equal 2. In the present example L=10 cm and d=0.2 mm so L/d=500

According to the invention, another way to define d and L could be to indicate that d and L depend notably on the energy of the particle emitted by a particular isotope emitted by the source of radiation to analyze. More particularly, d could be very lower (e.g. at least 10 times lower) than r (range of the particle in the fiber medium) and L could be very greater (e.g. at least 10 times greater) to r at the same time For example, the scintillating fibers (2) could be the products commercialized under the trademarks Kururay or Bicron.

The fiber(s) (7) of the probe has (have) a directional sensitivity which is shown in FIG. 2. Axially directed particles deposit much more ionization losses than transverse ones The directional sensitivity of single fiber [FIG. 2a] and of separate fibers [FIG. 2b] could be preserved by stopping material (8) (colored dark in the drawing).

This stopping material (8) forms a cladding for the single fiber [FIG. 2a] and also an interstitial material for the separate fibers [FIG. 2b].

The photo-sensor SiPM (1) has a low cost, a low operating voltage (25-50 V), a high internal gain (up to $10^6$), and a single-photon sensitivity at room temperature.

The electronic control box (3) can include a system for processing the signals produced by the probe and optionally by the additional detector(s), this system comprising:
at least one of the means (a), (b), (c) (d) & (e) as defined above;
optionally means of amplifying these electrical signals,
optionally at least one comparator,
optionally at least one analogue-to-digital converter,
optionally means of selecting the coincident detection signals, including:
elements for discriminating between the electrical signals to be processed according to a Compton electron detection energy threshold S, i.e. according to the intensity of the electrical signals,
and/or elements for discriminating between the electrical signals to be processed according to their length (duration),
at least one electronic module for sorting the coincident detection signals,
means of counting the selected signals.

The electronic control box (3) can also include front-end electronics, power supplies, data acquisition and user interface units, can contain inputs for as many probes as needed for a particular application The photo-sensor SiPM (1) transforms in (a) electrical signal(s) ($SL_{oe}$) the scintillation light output ($SL_{oe}$) generated by the charged or neutral particles having entered and interacted with the scintillating fiber(s) and emitted at least partially at the opposite end (outlet end) of the detection rod.

The electrical signal $SL_{oe}$ is compared with a electrical signal corresponding to a threshold $SL_t$ The FIG. 3 shows an example of the use of the probe in a medical diagnostic, preoperative or intraoperative procedure. The optional second detector, operated in coincidence, in this case is positioned slab under the patient.

The invention claimed is:

1. Method of detecting, locating and/or analyzing a radioactive source(s) emitting charged or neutral particles in a material, particularly a biological tissue, characterized in that it consists essentially in:
placing one of the ends ($1^{st}$ end) of at least one detection rod made of at least one scintillating fiber (preferably a substantially straight one), on or near the surface of the material to be analyzed, so as to enable the charged or neutral particles to enter the scintillating fiber(s); said scintillating fiber(s) having a ratio L (Length)/r (range of the charged particles emitted by the source, or produced in surrounding medium as secondary products) greater than or equal to 2, preferably greater than or equal to 10, and more preferably comprised between 50 and 200 and a ratio d (diameter)/r lower than or equal to 1, preferably comprised between 0.01 and 1, more preferably between 0.05 and 0.5, and more preferably between 0.1 and 0.3;
scanning said surface with the detection rod;
collecting the scintillation light output ($SL_o$) generated by the charged or neutral particles having entered and interacted with the scintillating fiber(s) and emitted at least partially at the opposite end ($2^{nd}$ end or outlet end) of the detection rod, wherein the particles comprise photons which interact with the scintillating fiber(s) with emission of secondary electrons which are the particles actually detected;
selecting at least some of the signals of scintillation light corresponding to $SL_o$;
comparing $SL_o$ with a minimum limit $SL_t$ related to a limit for the Compton scattering angle, in order to discriminate the photons which are essentially aligned with the fiber(s);
correlating $SL_o$, and the selected signals, to (a) the presence of a source of radiation located in the mass of the material to be analyzed;
(b) the intensity of the selected signals to the mass and/or the volume of the detected source of radiation, for the purpose of analysis; or (c) both (a) and (b); and
communicating these data to the user.

2. Method according to claim 1 wherein the scintillating fiber(s) has a ratio L (Length)/d (diameter) greater than or equal to 2, preferably greater than or equal to 5, and more preferably comprised between 10 and 500.

3. Method according to claim 1 comprising a step consisting in converting the optical signals of scintillation light output into electric signals.

4. Method according to claim 1 wherein the radioactive source(s) is (are) a cluster(s) of radioactive substances either moving or staying in the same place.

5. Method according to claim 1 wherein the radioactive source(s) emit(s) charged and/or neutral radiations, particularly positron or electron radiations.

6. Method according to claim 1 wherein the material is a biological tissue, which is radiolabeled with a positron or electron emitter.

7. Method according to claim 1 wherein the material is a biological tissue, wherein the radioactive source(s) is(are) preferably a tumor(s), radiolabeled with radiopharmaceutical compounds and wherein the data communicated to the user are limited to the information according to which a source of radiation with a higher activity than the surroundings tissues is or is not detected, with the exception of any deductive medical or veterinary decision (purely intellectual exercise) such as diagnostic conclusions.

8. Method according to claim 1, characterized in that the radioactive marker of the material to be analyzed is selected from any molecules labeled with positron emitters from the group comprising $^{18}F$, particularly $^{18}F$-labeled 2-fluorodeoxyglucose (FDG), $^{15}O$, $^{11}C$, $^{13}N$, $^{124}I$, $^{126}I$, $^{77}Br$, $^{64}Cu$, $^{178}Ta$, $^{108}Ag$, $^{96m}Tc$, $^{88}Y$, $^{81m}Rb$, $^{68}Ga$, $^{66}Ga$, $^{63}Zn$, $^{65}Zn$, $^{58}Co$, $^{56}Co$, $^{52}Fe$, $^{52}Mn$, $^{52m}Mn$ $^{26}Al$, $^{22}Na$ and mixtures thereof.

9. Method according to claim 1 comprising:
comparing $SL_o$ with a threshold $SL_t$ corresponding to a given quantity of energy $E_t$ deposited by the particles on a length $l_t$ ($l_t$ being lower than or equal to the range r of said particles) in the scintillating fiber, said length $l_t$ being correlated to a discrimination angle $\alpha_t$ which is the angle between the axis of the scintillating fiber and the direction of the particles entering the scintillating fiber;
selecting the signals of scintillation light for which $SL_o$ is greater than or equal to $SL_t$, said selected signals corresponding essentially to the particles entering the scintillating fiber(s) in a substantially axial direction, that is to say eliminating the particles:
which angle $\alpha_p$, that is the angle between the axis of the scintillating fiber and the direction of the particles entering the scintillating fiber, is greater than $\alpha_t$ ($\alpha_p > \alpha_t$),
then which length $l_p$, is lower than $l_t$ ($l_p < l_t$)
and thus finally which quantity of energy $E_p$ deposited by the particles on a length $l_p$ in the scintillating fiber is lower than $E_t$ ($E_p < E_t$);
correlating the selected signals to the presence of a source of radiation located in the mass of the material to be analyzed and substantially in the axis of the detection rod.

10. Method according to claim 9 wherein $\alpha_t$ is lower than or equal to 45 ($\alpha_t \leq 45$), preferably lower than or equal to 30 ($\alpha_t \leq 30$), more preferably comprised between 0 and 10 ($0 \leq \alpha_t \leq 10$).

11. Device for detecting, locating and analyzing a radioactive source(s) emitting charged or neutral particles in a material, particularly a biological tissue, characterized in that it includes:
at least one probe comprising:
at least one detection rod made of at least one scintillating fiber (preferably a substantially straight one), through which the possible radioactive particles coming from the radioactive source(s) can enter the scintillating fiber(s) and so interact with the fiber(s) to generate scintillation light (SL), wherein the particles comprise photons which interact with the scintillating fiber(s) with emission of secondary electrons which are the particles actually detected, said scintillating fiber having a ratio L (Length)/r (range of the charged particles emitted by the source or produced in surrounding medium as secondary products) greater than or equal to 2, preferably greater than or equal to 5, and more preferably comprised between 10 and 200, and a ratio d (diameter)/r lower than or equal to 1, preferably comprised between 0.01 and 1, more preferably between 0.05 and 0.5, and more preferably between 0.1 and 0.3, the scintillating fiber comprising:
one $1^{st}$ end designed so as to be placed on or near the surface of the material to be analyzed and so as to scan said surface,
one body (preferably a substantially straight one) of length L and of diameter d, and capable, on the one hand, to interact with the particles coming from the radioactive source(s) to generate scintillation light (SL), and, on the other hand, to channel SL up to the $2^{nd}$ end,
one $2^{nd}$ end or outlet end through which possible SL can be at least partially emitted;
at least one compact photosensor (preferably directly connected to the tip of the detection rod corresponding to the $2^{nd}$ end(s) of the scintillating fiber(s), for collecting the possible scintillation light output ($SL_o$) and transforming it in (a) electrical signal(s) ($SL_{oe}$),
means for comparing $SL_o$ with a minimum limit $SL_t$ corresponding to a maximum accepted scattering angle between the incoming photon and the emitted electron,
means for selecting at least some of the signals of scintillation light corresponding to $SL_{oe}$;
means for correlating $SL_{oe}$ and the selected signals to (a) the presence of a source of radiation located in the mass of the material to be analyzed;
(b) the intensity of the selected signals to the mass and/or the volume of the detected source of radiation, for the purpose of analysis; or (c) both (a) and (b); and
means for communicating these data to the user.

12. Device according to claim 11 wherein the radioactive source(s) is (are) cluster(s) of radioactive substances either moving or staying in the same place.

13. Device according to claim 11 wherein the material is a biological tissue or object, which is radiolabeled with a positron or electron emitter.

14. Device according to claim 11 further comprising means for selecting the $SL_o$ lower than or equal to $SL_{max}$.

15. Device according to claim 11 wherein the fiber(s) is composed of a scintillating part optically connected to a transparent fiber with the purpose to extend its length without increasing sensitivity to background radiation.

16. Device according to claim 11 wherein the detection rod of the probe includes either one or a set of parallel fibers, preferably interspaced by a bulk material.

17. Device according to claim 11 wherein the photosensor is a single-photon sensitive avalanche photodiode operating in 'Geiger mode', i.e. above breakdown, said photosensor being preferably selected in the group of Silicon Photo-Multiplier (SiPM) comprising: the Metal-Resistive Layer-Silicon Avalanche Photo Diode (MRS-APD), the Avalanche Photo Diode operating in Geiger mode (APDG), the Multipixel Avalanche Photodiode (MAPD) and the Single Photon Avalanche Diode (SPAD) array.

18. Device according to claim 11 wherein the $1^{st}$ end of the scintillating fiber(s) or of the detection rod comprise means for reflecting the scintillating light towards the $2^{nd}$ or outlet end of said scintillating fiber(s).

19. Device according to claim 11, wherein the material is a biological tissue or object radiolabeled with radiopharmaceutical compounds or radio-tracers and wherein the device is used in the purpose of any biomedical static or dynamic study, of non-invasive intra-cavity, transcutaneous or intravascular detection of radiolabeled biological tissues or radioactive tracers used for any bio-medical diagnostic, surgical, therapeutic or research procedures, including pharmacological, oncological, cardiological, neurological and neurosurgical ones.

20. Device according to claim 11, wherein the material is a biological tissue, wherein the radioactive source(s) is(are) a tumor(s), radiolabeled with radiopharmaceutical compounds and wherein the device is used in the purpose of pre-operative medical diagnostics or intra-operative tumor localization in surgery, preferably radio-guided surgery.

21. Device according to claim 20 capable to detect and/or locate tumoral areas with a size preferably less than or equal to 20 mm and particularly preferably less than or equal to 5 mm.

22. Device according to claim 11 wherein (a) the means for comparing $SL_{oe}$ with a threshold $SL_t$, (b) the means for selecting the signals $SL_{oe}$, (c) the means for correlating the selected signals to the presence of a source of radiation, (d) the means for correlating the intensity of the selected signals to the mass and/or the volume of the detected source of radiation and/or (e) the means for communicating these data to the user (preferably in visual and/or audible form), are integrated in a electronic control box which is structurally independent and can be distant from the probe, said electronic control box being connected to the probe by means of transporting the detection electrical signal(s) ($SL_{oe}$).

23. Device according to claim 22 wherein one or several probes are connected with the electronic control box by means of a long and flexible electrical cable.

24. Device according to claim 22 wherein the electronic control box includes a system for processing the signals produced by the probe and optionally by the additional detector(s), this system comprising:
at least one of the means (a), (b), (c) (d) & (e) as defined in claim 22;
means of amplifying these electrical signals,
at least one comparator,
at least one analogue-to-digital converter,
means for selecting the coincident detection signals, including;
(a) elements for discriminating between the electrical signals to be processed according to a Compton electron detection energy threshold S, i.e. according to the intensity of the electrical signals,
(b) elements for discriminating between the electrical signals to be processed according to their length (duration), or
(c) both (a) and (b); and
at least one electronic module for sorting the coincident detection signals,
means for counting the selected signals.

25. Device according to claim 22 wherein the electronic control box is capable to provide information on the presence of source of radiations in different positions inside or outside the material under analysis.

26. Device according to claim 11 wherein the radioactive source(s) emit(s) charged and/or neutral radiations, particularly positron radiations.

27. Device according to claim 26 comprising at least one additional detector (preferably comprising a slab) which is intended to be placed opposite to the detection rod of the probe with respect to the material to be analyzed, and operated in coincidence with the detection rod of the probe for background discrimination in case where the source of radiation is a positron emitter.

28. Device according to claim 27 wherein the source of radiation emits positrons and comprising:
at least one additional detector (preferably comprising a slab) which is intended to be opposite to the detection rod with respect to the material to be analyzed, each of the two detectors being capable of detecting a Compton electron produced, according to the Compton scattering mechanism, from interaction of one of the two incident photons resulting from annihilation between a positron emitted by the mass of material to be analyzed, and an electron;
means for selecting the coincident detection signals, namely the signals for each of which the detection of a Compton electron in a detector coincides temporally with the detection of a Compton electron in the other opposite detector;
means for counting the selected signals so as to acquire data correlated with the amount of positrons emitted by the mass of material to be analyzed, said means for selecting and means for counting belonging to a system for processing the signals produced by the detectors.

29. Device according to claim 11 comprising:
means for comparing $SL_{oe}$ with a threshold $SL_t$ corresponding to a given quantity of energy $E_t$ deposited by the particles on a length $l_t$ ($l_t$ being lower than or equal to the range r of said particles) in the scintillating fiber, said length $l_t$ being correlated to a discrimination angle $\alpha_t$ which is the angle between the axis of the scintillating fiber and the direction of the particles entering the scintillating fiber,
means for selecting the signals of scintillation light for which $SL_{oe}$ is greater than or equal to $SL_t$, said selected signals corresponding essentially to the radioactive particles entering the scintillating fiber(s) in a substantially axial direction, that is to say eliminating the particles:
which angle $\alpha_p$, that is the angle between the axis of the scintillating fiber and the direction of the particles entering the scintillating fiber, is greater than $\alpha_t$ ($\alpha_t > \alpha_p$)
then which length $l_p$ is lower than $l_t$ ($l_p < l_t$),
and thus finally which quantity of energy $E_p$ deposited by the particles on a length $l_p$ in the scintillating fiber is lower than $E_t$ ($E_p < E_t$);
and means for correlating the selected signals to the presence of a source of radiation located in the mass of the material to be analyzed and substantially in the axis of the detection rod.

30. Device according to claim 29 wherein $\alpha_t$ is lower than or equal to 45 ($\alpha_t = <45$), preferably lower than or equal to 30 ($\alpha_t = <30$), more preferably comprised between 0 and 10 ($0 = <\alpha_t = <10$).

31. Device according to claim 29 wherein the scintillating fiber(s) has a ratio L (Length)/d (diameter) greater than or equal to 2, preferably greater than or equal to 5, and more preferably comprised between 10 and 500.

32. Device according to claim 31 wherein the external surface of the scintillation fiber(s) comprise(s) at least one cladding designed so as to capture the scintillating light SL which is then at least partially channeled towards the outlet end of the scintillation fiber(s).

* * * * *

UNITED STATES PATENT AND TRADEMARK OFFICE
CERTIFICATE OF CORRECTION

| | |
|---|---|
| PATENT NO. | : 8,401,621 B2 |
| APPLICATION NO. | : 12/300175 |
| DATED | : March 19, 2013 |
| INVENTOR(S) | : Stefano Buono et al. |

It is certified that error appears in the above-identified patent and that said Letters Patent is hereby corrected as shown below:

In the Claims:

Col. 15, Claim 8, Line 21, delete "$^{96m}Tc$" and replace witth --$^{95m}Tc$--;

Col. 17, Claim 24, Line 35, delete the word "optionally".

Signed and Sealed this
Second Day of July, 2013

Teresa Stanek Rea
*Acting Director of the United States Patent and Trademark Office*